US005085650A

United States Patent [19]

Giglio

[11] Patent Number: 5,085,650

[45] Date of Patent: Feb. 4, 1992

[54] GYNECOLOGICAL URETHRAL SUPPOSITORY

[76] Inventor: Frank A. Giglio, 1265 Nottingham La., Beaumont, Tex. 77706

[21] Appl. No.: 424,707

[22] Filed: Oct. 20, 1989

[51] Int. Cl.[5] ............ A61F 15/00

[52] U.S. Cl. ............ 604/288

[58] Field of Search ............ 604/285-288

[56] References Cited

U.S. PATENT DOCUMENTS

| | | | |
|---|---|---|---|
| 794,233 | 7/1905 | Kistler | 604/288 |
| 1,218,478 | 3/1917 | Sappington | 604/286 |
| 1,737,949 | 12/1929 | Schaaf | 604/287 |
| 1,767,785 | 6/1930 | Sushko | 604/288 |
| 3,126,887 | 3/1964 | Gordon | 604/288 |
| 3,689,514 | 9/1977 | Neissner et al. | 604/48 |
| 3,840,010 | 10/1974 | Giglio | 604/288 |
| 4,344,968 | 8/1987 | Aoda et al. | 604/288 |
| 4,460,360 | 7/1984 | Finegold | 604/288 |

FOREIGN PATENT DOCUMENTS

| | | | |
|---|---|---|---|
| 1475877 | 4/1967 | France | 604/288 |
| 17321 | of 1911 | United Kingdom | 604/288 |

OTHER PUBLICATIONS

Bent, Alfred E. M.D., "Urethral Syndrome" Diagnosis and Management, *Medical Aspects of Human Sexuality*, pp. 84-86, Mar. 1989.

*Primary Examiner*—Stephen C. Pellegrino
*Assistant Examiner*—Ralph A. Lewis
*Attorney, Agent, or Firm*—Michael A. O'Neill

[57] ABSTRACT

A gynecological urethral suppository includes a shaft, a bulbous head secured to one end of the shaft and a conical tail secured to the other end. The head comprises an outwardly curved retention surface and a gradually inwardly curved insertion surface. The tail includes an outwardly tapered retaining surface and a flat base, and has a maximum diameter that is greater than the maximum diameter of the head. The unique structure of the urethral suppository facilitates retention of the urethral suppository in the uretha such that medicament may be topically applied to the urethra, the urethral meatus, the bladder trigone, the bladder itself, and the ureters in an effort to cure urethral syndrome, trigonitis and posterior urethritis.

1 Claim, 1 Drawing Sheet

FIG.1
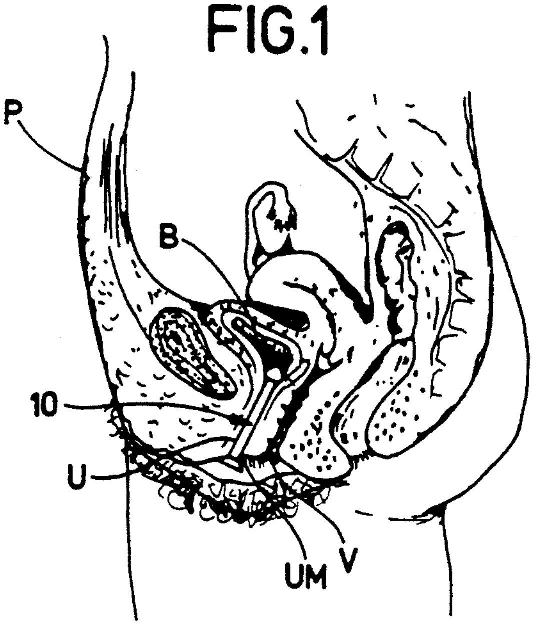
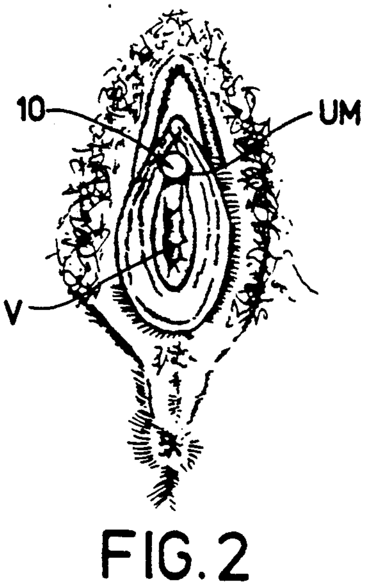
FIG. 2
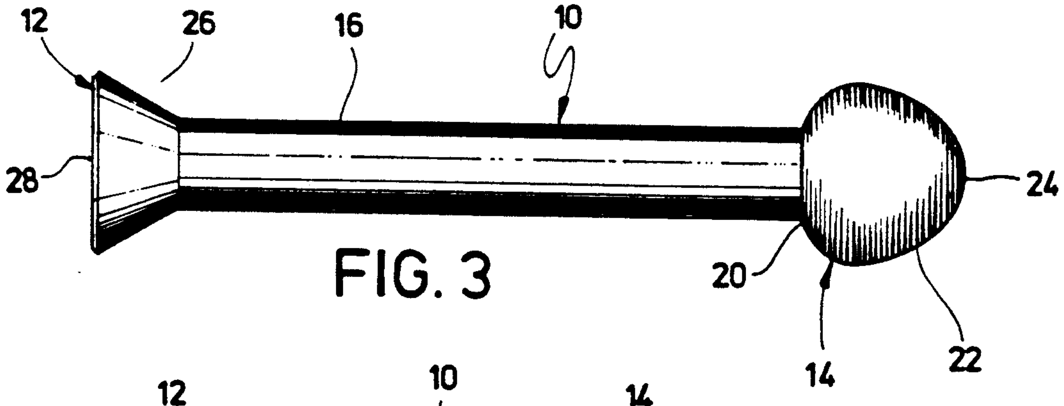
FIG. 3
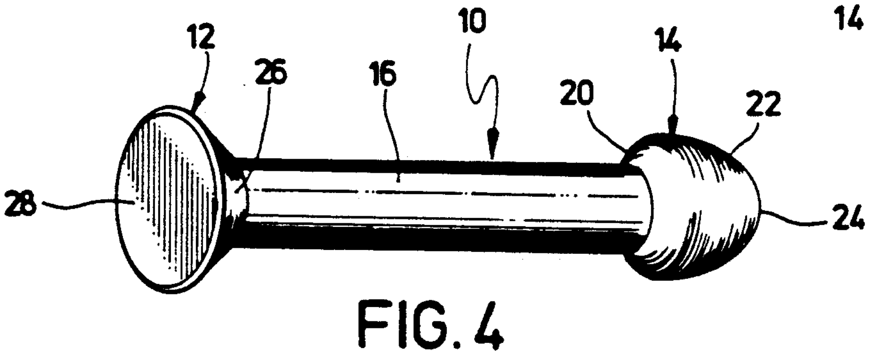
FIG. 4

GYNECOLOGICAL URETHRAL SUPPOSITORY

TECHNICAL FIELD

This invention relates to a suppository, and more particularly to a urethral suppository for use in the treatment of urethral syndrome, trigonitis and posterior urethritis.

BACKGROUND AND SUMMARY OF THE INVENTION

In the treatment of urethral syndrome, trigonitis and posterior urethritis, topical application of medicament is the preferred means of treatment. Due to the remote location of the tissues affected by these ailments, however, topical application has heretofore been impossible or ineffective. For example, urethral suppositories used in the past for treatment of these ailments have slipped into the bladder or have been expelled due to internal pressure. The present invention presents a unique design for the gynecological urethral suppository which facilitates topical application of the desired medicament on the urethra itself, as well as on the bladder trigone, the ureters, the periurethra, the urethral meatus and the bladder, while facilitating comfortable retention of the suppository in the urethra during use.

Urethral syndrome is a complex of persistent, irritative lower urinary tract symptoms without evidence of bacteriologic infection or obvious bladder or urethral abnormality. The reported incidence of urethral syndrome among adult women is 20% to 30%. The most common presenting symptoms are urinary frequency, urgency and dysuria; other frequent symptoms include suprapubic pressure, tenderness and dyspareunia. By contrast, urinary incontinence and nocturia are uncommon complaints.

The diagnosis of urethral syndrome is based on the presenting history of chronic, irritating lower urinary tract symptoms without evidence of bacteriologic infection. In the course of physical examination, the external genitalia, urethra, and urethral meatus are inspected. Graduated urethral sounds (available in sizes 12-38 French) may be used to calibrate the urethra. The normal urethra measures 22-28 French. Urodynamic assessment may be included.

Past treatment of urethral syndrome has relied on the administration of oral medication, since effective topical application was impractical due to the remoteness of the affected tissues and the ineffectiveness of past attempts to employ urethral suppositories.

In accordance with the present invention, a urethral suppository is provided that overcomes the difficulties experienced with the past use of oral medication and prior urethral suppositories. The preferred embodiment of the invention comprises a urethral suppository including a bulbous head including a gradually inwardly curved surface that eases insertion of the suppository and an outwardly curved surface that facilitates comfortable retention. The bulbous head further facilitates topical application of medication to the bladder trigone, where the urethra joins the ureters to facilitate passage of urine from the bladder.

The urethral suppository further comprises an enlarged conical tail that facilitates comfortable retention of the urethral suppository, while successfully administering medication to the urethral meatus. The bulbous head and conical tail of the urethral suppository are joined by a narrow shaft which topically applies medicament to the interior wall of the urethra. Preferably, the urethral suppository consists entirely of a medicament that melts or dissolves during the use thereof.

The protocol employing the gynecological urethral suppository herein disclosed will include a seven-day treatment of twice daily insertion of the urethral suppository. The primary treatment for a perimenopausal patient is a urethral suppository comprising one percent Hydrocortisone, 0.007 percent Diethylstilbesterole, and two percent Lydocaine suspended in a base, such as Polyethylene Glycol. Hydrocortisone is included in the medicament in an effort to counteract chronic periurethral gland inflammation and inhibit deposition of collagen in the urethrovaginal septum. Lydocaine is included as a topical anesthetic.

BRIEF DESCRIPTION OF THE DRAWINGS

A more complete understanding of the invention may be had by referring to the following detailed description when taken in conjunction with the drawing wherein:

FIG. 1 is a schematic illustration of the use of the present invention;

FIG. 2 is a detailed schematic front view illustration of the use of the present invention;

FIG. 3 is a side view of the present invention; and

FIG. 4 is a perspective view of the present invention.

DETAILED DESCRIPTION

Referring now to the drawing, and particularly to FIGS. 3 and 4 thereof, there is shown a urethral suppository 10 comprising the present invention. The urethral suppository 10 includes a relatively long, relatively small shaft 16, a bulbous head 14 secured to one end of the shaft 16 and a conical tail 12 secured to the other end. The suppository 10 is comprised entirely of a medicament and is circular in cross section throughout its length.

The bulbous head 14 includes an outwardly curved retention surface 20 that extends from the shaft 16 and a gradually inwardly curved insertion surface 22 that extends from the surface 20 to a rounded nose 24. The shape of the surfaces 20 and 22 is important in that the insertion surface 22 facilitates easy insertion of the suppository 10 and in that the retention surface 20 facilitates comfortable retention of the urethral suppository. It should be noted that the intersection between the retention surface 20 and the insertion surface 22 does not comprise a sharp edge or corner. In and of itself, this greatly reduces the discomfort involved in the use of urethral suppositories employing the present invention.

The conical tail 12 includes an outwardly tapered retention surface 26 that extends from the shaft 16 to a flat base 28. The portion of the surface 26 located adjacent the base 28 is of a substantially larger diameter than the maximum diameter of the head 14 and is employed in the suppository 10 to medicate the urethral meatus and the posterior portion of the urethra. The flat base 28 is also important in that it facilitates the positioning of the suppository 10 on a bedside table prior to insertion, and in that it facilitates insertion of the suppository 10 by providing an outwardly facing thrust surface.

It will be understood that the dimensions of the various portions of a suppository employing the present invention are very important to the successful practice of the invention. That is, the suppository must be of such a size that it is retained in the urethra and yet must not be of such a size that it causes undue discomfort during insertion and use. It has been found that the ideal dimensions for a suppository employing the present invention are as follows:

| | | | |
|---|---|---|---|
| A. | Shaft | Diameter | 5.0 mm |
| | | Axial Length | 37.0 mm |
| B. | Head | Diameter | 8.0 mm |
| | | Axial Length | 8.0 mm |
| C. | Base | Diameter | 11.2 mm |
| | | Axial Length | 5.0 mm |

Suppositories employing the present invention preferably consist entirely of a medicament that melts or dissolves during use. For example, a medicament comprising a suitable vehicle, such as Polyethylene Glycol, and suitable medicinal substances such as Hydrocortisone, Diethylstilbesterole and Lydocaine dispersed throughout the vehicle may be used.

The use of urethral suppositories employing the present invention is illustrated in FIGS. 1 and 2. A urethral suppository is positioned in the urethra U of a patient P by pushing on the base of the urethral suppository. Insertion of the suppository is greatly facilitated by the shape of the insertion surface of the bulbous head, which renders the insertion of the suppository relatively easy and painless. When in place, the suppository is retained relatively painlessly in the urethra due to the unique shape of the urethral suppository employing the bulbous head in concert with the conical tail. The conical tail prevents the passage of the urethral suppository into the bladder B, while facilitating application of the medicament to the urethral meatus UM. The bulbous head anchors the suppository at the bladder trigone both to facilitate application of the medicament thereto and to prevent its expulsion.

During the use of the urethral suppository 10, medicament is topically applied to the urethral meatus, UM the urethra, U the bladder trigone, and thereby to the bladder B and ureters as well. The unique design of the urethral suppository 10 facilitates improved delivery of medicament to the surfaces of substantially all of the tissues affected by urethral syndrome, trigonitis and posterior urethritis.

Although a specific embodiment of the invention is illustrated in the drawing and described herein, it will be understood that the invention is not limited to the embodiment disclosed, but is capable of rearrangement, modification and substitution of parts and elements without departing from the spirit of the invention.

I claim:

1. A urethral suppository comprising:

a relatively long, relatively small diameter shaft;

a bulbous head extending from a rounded nose through a relatively gradually outwardly curving insertion surface having an axial length equaling about two thirds of the overall length of the head and a relatively sharply curving retention surface extending from the intersection with the insertion surface which is the maximum diameter of the head to an intersection with the shaft, the intersection between the retention surface and the insertion surface not comprising a sharp edge or corner;

a conical tail including an outwardly tapered retaining surface extending from the shaft to a base having a diameter substantially greater than the maximum diameter of the bulbous head;

said shaft, head, and tail comprising a unitary structure and being formed entirely from a medicament; and said shaft, head, and tail characterized by the following dimensions:

| | | | |
|---|---|---|---|
| A. | Shaft | Diameter | 5.0 mm |
| | | Axial Length | 37.0 mm |
| B. | Head | Diameter | 8.0 mm |
| | | Axial Length | 8.0 mm |
| C. | Base | Diameter | 11.2 mm |
| | | Axial Length | 5.0 mm |

* * * * *